006# United States Patent [19]

Tsujita et al.

[11] Patent Number: 5,049,375

[45] Date of Patent: Sep. 17, 1991

[54] ORAL COMPOSITIONS CONTAINING COLLOIDAL FLUORIDE

[75] Inventors: Satoshi Tsujita; Manabu Tonomura, both of Tochigi; Shigeto Kayane, Wakayama; Takashi Imamura, Chiba, all of Japan

[73] Assignee: Kao Corporation, Tokyo, Japan

[21] Appl. No.: 527,776

[22] Filed: May 24, 1990

[30] Foreign Application Priority Data

May 31, 1989 [JP] Japan .................................. 1-138036
May 31, 1989 [JP] Japan .................................. 1-138037

[51] Int. Cl.$^5$ ........................ A61K 7/18; A61K 33/16
[52] U.S. Cl. .................................... 424/52; 424/440; 424/441; 424/673; 424/675
[58] Field of Search .......................................... 424/52

[56] References Cited

U.S. PATENT DOCUMENTS 4,177,258 12/1979 Gaffar et al. .
4,565,691 1/1986 Jackson .
4,606,912 8/1986 Rudy et al. .

FOREIGN PATENT DOCUMENTS

0200323 3/1986 European Pat. Off. .
0233059 2/1987 European Pat. Off. .
0263638 9/1987 European Pat. Off. .
47-39642 12/1972 Japan .
51-91339 8/1976 Japan .
57-212112 12/1982 Japan .
58-219107 12/1983 Japan .
2188548 4/1987 United Kingdom .

Primary Examiner—Shep K. Rose
Attorney, Agent, or Firm—Birch, Stewart, Kolasch & Birch

[57] ABSTRACT

A colloidal solution comprises a fluoride(s) being difficultly soluble in water comprises colloidal particles of the fluoride having a particle size of 0.005 to 1 micron, said fluoride having a fluoride ion concentration of 1 to 10,000 ppm in the state of saturation.

14 Claims, 4 Drawing Sheets

ORAL COMPOSITIONS CONTAINING COLLOIDAL FLUORIDE

The present invention relates to a colloidal fluoride solution and a process for producing said solution. In particular, the present invention provides a colloidal solution of a difficultly soluble fluoride which gives a fluoride ion concentration of 1 to 10,000 ppm when dissolved in water. The colloid of the present invention can be used alone or in the form of an oral composition in such an amount that the fluorine content thereof will be 10 to 100,000 ppm in combination with other substances for preventing the tooth from decaying.

The present invention relates to an oral composition characterized in that fluorine and calcium contained therein are at least partially reacted with each other to form a colloidal fluoride in the presence of a peptizer such as a suitable saccharide derivative to enhance the availability of fluorine for the teeth and to improve its effect of preventing the tooth from decaying.

[Prior Art]

Various compounds were proposed as components effective in preventing teeth from decaying. Among them, those which are deemed to be the most effective are fluorides such as sodium fluoride, sodium monofluorophosphate and stannous fluoride. The fluorides are effective mainly due to the fluoride ions which improves the acid resistance of the teeth and accelerate recalcification of a decayed tooth in its early stage wherein the decalcification has proceeded only slightly. The effect of improving the acid resistance of the teeth is thought to be due to the fact that the fluoride ions are incorporated into a crystal lattice of hydroxyapatite which is the main constituent of tooth enamel or, in other words, fluoride ions partially fluorinate hydroxyapatite and simultaneously repair the lattice irregularities. The recalcification is a reaction for recovering or substantially recovering the hydroxyapatite, which was shortened, modified or lost by the decalcification of the enamel, by a reaction reverse to the decalcification to inhibit the decay of the tooth. This reaction ordinarily proceeds in addition to the decalcification and is remarkably accelerated in the presence of a fluoride ion.

These effects are quite peculiar to the fluoride ion and there is no substitute for this ion. Fluorides are thus added to tap water, used in the form of tablets to be crushed with the teeth, added to foods, applied to the tooth surface or added to mouth-washes or dentifrices.

As for the extent of the effect of the fluorides for preventing the tooth from decaying, it is 50 to 65% when it is added to tap water, 30 to 40% when it is applied to the tooth surface, and 20 to 50% when it is used in the form of a mouth-wash or dentifrice. Although the effect of the iodides is far more remarkable than that of other agents for preventing the tooth from decaying, complete prevention of the decaying is still ideal. From this point of view, the effect of the fluorides is yet insufficient. In particular, when the fluoride is not orally administered but directly applied to the tooth (local application) as in the case of a mouth wash or dentifrice, the effect thereof for preventing the decay of the tooth is small. Thus it leaves much room for improvement.

Under these circumstances, investigations are in progress for the purpose of finding a new composition for improving the effect of the fluoride, a new method of treating the teeth or a new fluorine compound.

Particularly with respect local application, the efficiency of fluorine uptake is low and a large amount of fluorine is disgorged without exhibiting any effect, so that various investigations are in progress for increasing the fluorine uptake.

In successful investigations, sodium fluoride acidified with phosphoric acid is used. In this case, phosphoric acid is used for increasing the fluorine uptake. This agent has been already widely used.

Recently, investigations were made for the purpose of incorporating 1,500 to 2,000 ppm (1.5 to 2 times as high as the ordinary concentration) of fluorine into a dentifrice in order to increase the fluorine uptake. Supposedly this method is effective.

The mechanism of exhibiting such a remarkable effect can be explained as follows: since the fluoride is locally applied for only a very short time, only a very small amount of the fluoride is used for the direct fluorination of the tooth and the reset acts to disintegrate part of the tooth to form calcium fluoride, which is dissolved in the saliva to release fluoride ions which fluorinate the tooth. When sodium fluoride acidified with phosphoric acid or a fluoride of a high concentration is used for the treatment, calcium fluoride is formed in a large amount to indirectly increase the effect of reinforcement of the tooth.

However, on the other hand, the tooth must be partially disintegrated in the treatment with the acidic sodium fluoride or the fluoride of a high concentration, so that some problems may occur during the application for a long period of time. Further, the acute toxicity of fluorine is by no means low, and the increase of the fluorine concentration is undesirable when it is taken by mistake.

Another expected method of accelerating the fluorine uptake comprises using various metallic ions in combination with the fluoride. For example, aluminum ion and calcium ion [J. Kyushu Dental Soc., 4 (1): 247 to 259] and lanthanum [Jap. J. Pedodontics, 25 (1): 1 to 11] have the effect of accelerating the fluorine uptake.

The mechanism is as follows: the insoluble fluoride thus formed is adsorbed on apatite. When the metallic ion is a calcium ion, the insoluble fluoride is the same calcium fluoride. In principle, this is similar to the treatment with the fluoride of a high concentration. However, the enamel is not disintegrated unlike the treatment with the fluoride of a high concentration.

Another subsidiary effect, in addition to the effect of acceleration of the fluorine uptake, of the metallic ions incorporated therein has also been known.

For example, it is known that a calcium ion has an effect of accelerating the recalcification and that a combination thereof with the fluorine-containing agent is effective. Examples of the combinations are disclosed in Japanese Patent Laid-Open Nos. 039642/1972 (Beecham Group) and 091339/1975 (Procter & Gamble) and some of them are available on the market.

It is known that titanium, etc. have an effect of improving acid resistance owing to their coating effect.

Therefore, a composition comprising a combination of a fluoride ion with a metallic ion is expected to be quite useful.

However, the composition comprising the combination of a fluoride ion with a metallic ion has many problems to be solved when it is practically used.

Fluorides of calcium, magnesium, strontium, lanthanoids such as lanthanum, molybdenum, manganese, aluminum and indium having the effect of preventing the tooth from decaying are insolbule or difficultly soluble in water. When an aqueous solution of such a fluoride is left to stand for a while, it precipitates and almost loses its reactivity to make it impossible to realize a high fluorine uptake or to exhibit the ordinary effect of fluorides.

Under these circumstances, investigations are in progress on the formulation of compositions capable of keeping the remarkable effect of the fluoride.

The processes heretofore proposed include, for example, a process disclosed in Japanese Patent Laid-Open No. 212112/1982 (Colgate-Palmolive) wherein aluminum and fluorine are kept in an oil layer and an aqueous layer, respectively, so that they are mixed at the time of use, a process disclosed in Japanese Patent Laid-Open No. 219107/1983 (Procter & Gamble) wherein most of calcium ions are protected by chelation and a process disclosed in Japanese Patent Laid-Open No. 091339/1975 (Procter & Gamble) wherein the pH of the solution is extremely lowered.

However, these processes have defects. Namely, the emulsion has a special texture which is unsuitable for giving pleasantness in its use. The chelation of calcium sacrifices the effect of the dentifrice. The low pH restricts the formulation and is not good for the tooth.

It is well known that fluorine has an effect of preventing the tooth from decaying. Fluorine is added in a very small amount (about 1 ppm) to tap water, incorporated into a dentifrice or mouth-wash (1,000 ppm or less) or applied to the surface of the tooth (about 10,000 ppm) by dentists. The effect of preventing the tooth from decaying is most remarkable when it is added to tap water and the effect is halved when it is incorporated into the dentifrice or mouth-wash. However, the incorporation thereof into the dentifrice or mouth-wash is desirable, since it is easy and economically advantageous. Thus one of the problems in the field of dental hygiene is an improvement of the above-described effect.

The essential action mechanism of the prevention of the tooth from decaying with the use of fluorine is that hydroxyapative (hereinafter referred to as HAP), a constituent of the enamel of the tooth, is converted into fluoroapative (hereinafter referred to as FAP) to improve the acid resistance of the tooth. The reaction of forming FAP from HAP slowly proceeds in the presence of fluoride ions of a low concentration. The addition of fluorine to tap water is quite effective, since fluorine taken into the body by drinking the tap water is continuously secreted into saliva in a very small amount over a long period of time to exhibit its effect on the tooth and cause the conversion of HAP to FAP. When fluorine is incorporated into a dentifrice, no conversion of HAP into FAP can be expected in a short time of brushing the teeth. However, it was found that when fluoride ions of a high concentration acted on the enamel of the tooth, HAP was partially decomposed at a relatively high reaction rate to form calcium fluoride on the surface of the tooth, and calcium fluoride thus formed after the brushing of the tooth was slowly dissolved to release fluoride ions to thereby cause the conversion of HAP into FAP. Therefore, the larger the amount of fluorine incorporated into the dentifrice, the larger the calcium fluoride deposited on the surface of the tooth and the more remarkable the effect. However, the upper limit of the fluorine content is regulated to be 1,000 ppm at present in due consideration of a risk of drinking it by mistake.

As described above, the fluoride ion contained in a dentifrice or mouth-wash forms calcium fluoride by the chemical reaction on the surface of the tooth, thereby deposited thereon, and then exhibits the effect of preventing the tooth from decaying after the conversion of HAP to FAP. Therefore, it is necessary to bring the fluoride ion to as high a concentration as possible into contact with the tooth for an as long as possible time when the tooth is brushed with the dentifrice. Since, however, the upper limit of the fluorine content in the dentifrice is regulated and the time of brushing the teeth cannot be prolonged, there remains a problem in that the uptake of fluorine by the teeth cannot be sufficiently increased.

[Summary of the Invention]

After investigations, the inventors have succeeded in colloidizing a difficultly soluble fluoride precipitate. On the basis of this finding, the inventors have succeeded in developing a composition comprising the colloid to increase the fluorine uptake by the tooth enamel. The fluorine thus taken up is then gradually released over a long period of time to exhibit an effect far superior to that of ordinary ones. The composition also has an excellent storage stability and the teeth can be effectively prevented from decaying with an oral composition containing this colloidal solution.

After intensive investigations made for the purpose of finding a new fluorine-containing agent having an excellent effect of supplying fluorine to the tooth, the inventors found that a colloidal dispersion of calcium fluoride formed by reacting fluoride ions with calcium ions exhibited a quite high adhesion to the tooth and a quite excellent effect of supplying fluorine to the tooth immediately after the reaction. However, it was also found that this effect was reduced as the colloidal calcium fluoride present in the dispersion aggregated to form a precipitate with the lapse of time.

After further intensive investigations made for the purpose of retaining the effect of the colloidal calcium fluoride for a long period of time, the inventors have found that when fluoride ions are reacted with calcium ions in the presence of a peptizer comprising a particular saccharide derivative, a colloidal fluoride having an extremely small particle diameter can be formed and it exhibits an extremely high adsorption on the tooth. Therefore, it can efficiently supply fluorine to the tooth to improve its resistance to decaying. Further, the colloid has a high stability and its effect lasts for a long period of time. The present invention has been completed by applying it in the production of an oral composition.

In the invention, a colloidal solution comprises the fluoride(s) being difficultly soluble in water comprises the colloidal particles of the fluoride having a particle size of 0.005 to 1 micron, said fluoride having a fluoride ion concentration of 1 to 10,000 ppm in the state of saturation.

The solution may further comprise the peptizer(s) to colloidize the fluoride.

The solution may comprise 1 to 100,000 ppm, based on the entire solution, of fluorine in the colloidal particles, 10 to 100 percent by weight of the fluorine contained in the entire solution being included in the colloidal particles.

The peptizer is preferably selected from polyolphosphoric acids, polyolsulfuric acids, polyolcarboxylic acids and salts of each before-mentioned acid.

The solution may comprise 1 to 95,000 ppm, based on the entire solution, of fluorine in the colloidal particles, 10 to 95 percent by weight of the fluorine contained in the entire solution being included in the colloidal particles. The colloidal particles of the fluoride may have a particle size of 0.005 to 1 micron.

The invention provides a process for preparing a colloidal solution of a fluoride(s) being difficultly soluble in water, which comprises the steps of mixing a water-soluble fluoride with a water-soluble cationic salt to form precipitates and then add a peptizer(s) to the precipitates to produce colloidal particles having a size of 0.005 to 1 micron.

Alternatively the invention provides a process for preparing a colloidal solution of a fluoride(s) being difficultly soluble in water, which comprises the steps of mixing an aqueous solution of a water-soluble fluoride with an aqueous solution of a water-soluble cationic salt to form precipitates, at least either of both solutions containing a peptizer(s), to produce colloidal particles having a size of 0.005 to 1 micron.

In the invention colloidal particles can be obtained by conducting the process as defined above and removing the water. They can be also obtained by removing water from the solution.

It is preferable that at least one of the fluorides is a water-soluble hydrofluoric acid and at least one of the salt is a water-soluble calcium salt.

The invention also provides for an oral composition comprising at least one water-soluble fluoride, a water-soluble cationic salt and at least one peptizer.

The composition is preferred to comprise 10 ppm or more of fluorine, more preferably from 10 ppm to 100,000 ppm of fluorine, most preferably from 150 ppm to 60,000 ppm of fluorine.

It is preferable that the composition comprises 1 mol part of the calcium, 0.01 to 100 mol parts of the fluorine and 0.01 to 100 mol parts of the saccharide, more preferably 1 mol part of the calcium, 0.1 to 10 mol parts of the fluorine and 0.1 to 10 mol parts of the saccharide.

The peptiers are preferably polyol phosphates, polyol sulfates, polyol carboxylates and salts of the before mentioned.

In the invention, up to 100 percent by weight of fluorine is experimentally recognized in the colloidal particles. A fluorine concentration may range from 10 to 100,000 ppm in the entire colloidal solution. Such a colloidal solution can be obtained by selecting a fluoride to give a fluorine ion concentration of 1 to 10,000 ppm in the state of saturation.

In the invention, the formation of colloid in the solution can be experimentally recognized by the following methods (1) to (4).

(1) The solution containing the three components, that is, the fluoride, the cationic salt and the peptizer, is found to have a lesser of an amount of precipitaes or a lesser of an amount of turbidity than a control solution containing no peptizer, but the other two.

(2) The solution is filtered with a microporous filter having a pore size of 0.8 micron and 8 to 9 ml of the filtrate is collected in a bottle and is centrifuged with a ultra-centrifuging apparatus, such as SCP70H, tradename of Hitachi, SRP70AT, 50,000 rpm, 20 hours, 15 degree C. Precipitates shows formation of colloid.

(3) The solution is filtered with a microporous filter and the filtrate is found to have particles of 0.005 to 1 micron in view of dynamic light scattering, for example with the use of DLS-700, tradename of Otsuka Denshi Co., Ltd.

(4) The solution is found to have particles of 0.005 to 1 micron by determination with a transmission electron microscope, Hitachi-7000. A test sample is prepared by filtering the sample with a microporous filter, placing the filtered sample on a carbon support membrane having 200A mesh, hydrophilically treated by JFC-1100 of Nippon Denshi, 500 V, 2 mA, 20s×3, removing water therefrom and negative-dyeing it with uranyl acetate.

Thus the present invention provides a colloidal fluoride solution prepared by dissolving a difficultly soluble fluoride, which gives a fluoride ion concentration of 1 to 10,000 ppm when dissolved in water, in the form of fine colloidal particles having a diameter of 0.01 to 1 $\mu$m in water.

Since the colloidal solution of the present invention contains a compound which causes precipitation in nature kept in a metastable state when it is subjected to a change, such as during application to the mouth, the metastable state is lost and the colloidal particles begin to precipitate and the precipitates thus formed deposit on the teeth. Since fluorine is contained in the colloidal particles, the deposit gradually releases fluorine. The higher the fluorine content of the particles, the better. From our experience, a fluorine content of at least 10 wt. % is effective.

Although the limit of the content of fluorine in the particles have not yet been elucidated, the highest content thereof recognized in the experiments was 95%.

According to experiments, the fluorine concentration of the entire colloidal solution can be 10 to 1,000,000 ppm.

Although the reasons for them have not yet been elucidated, supposedly they are related to the mechanism of the formation of the colloid.

Such a colloid is obtained by suitably selecting the difficultly soluble fluoride capable of giving a fluoride ion concentration of 1 to 10,000 ppm when dissolved in water.

The fluoride is desirably calcium fluoride, aluminum fluoride, magnesium fluoride, barium fluoride, titanium fluoride, strontium fluoride, indium fluoride or a lanthanoid fluoride such as lanthanum fluoride, or a compound containing such a component in its structure.

The peptizer is particularly effective in maintaining the stability of the colloid and adhesion thereof to, for example, the teeth.

The peptizer is desirably a compound having a structure of a polyolphosphoric acid such as glucose-1-phosphate, and glucose-6-phosphate, polyolsulfuric acid such as sucrose sulfate or polyolcarboxylic acid such as gluconic acid, or salts of each acid.

It has been found that the solubility of the fluoride in the solution is quite high. Particularly when a sugar phosphate is used, the solubility is high and a transparent colloidal solution containing up to 100,000 ppm (in terms of fluorine) of the fluoride can be obtained.

The amount of fluorine in the colloidal particles was 95,000 ppm (95% based on the whole colloidal solution).

Although it was expected that a higher concentration of the colloidal solution might bring about a higher effect, the solubility of sodium fluoride was at most 20,000 ppm in terms of fluorine, so that the above-mentioned colloidal solution is superior to the conventional one in this respect.

The colloidal solution of the fluoride intended in the present invention is produced desirably by the following processes:

i) a process which comprises mixing a soluble fluoride such as sodium fluoride with a soluble cationic salt such as calcium chloride in such amounts and ratio that a fluoride will be precipitated when water is added thereto, adding a suitable amount of water to the mixture, further adding a peptizer as soon as a precipitate is formed, and either agitating the mixture or treating it with an ultrasonic cleaning apparatus, ii) a process which comprises preparing both of an aqueous solution of a soluble fluoride such as sodium fluoride and an aqueous solution of a soluble cationic salt such as aluminum chloride, dissolving a peptizer in at least one of these aqueous solutions, mixing both solutions together and either agitating the mixture or treating it with an ultrasonic cleaning apparatus, iii) a process which comprises mixing a soluble fluoride with the peptizer of the present invention such as a salt of glycerophosphoric acid, e.g., calcium salt thereof, adding water to the mixture, and either agitating the mixture or treating it with an ultrasonic cleaning apparatus, and iv) a process which comprises isolating the formed colloid in solid form by ultra-centrifugation, drying at a reduced pressure or addition of an alcohol and dissolving the dry colloid thus obtained again in water to give a sol-form colloidal solution.

The colloidal solutions of the difficultly soluble fluoride produced by each of the abovedescribed processes have the same physical and chemical properties and they are not different from one another depending on the processes. Namely, no difference can be found in the properties such as viscosity, electric conductivity, light scattering and results of elementary analysis.

Since the above-described processes are nothing but the examples of the production processes, any process wherein an insoluble or difficultly soluble fluoride is formed and simultaneously or thereafter a peptizer is added thereto to form the colloidal solution may be employed in the present invention.

Although the temperature in the process ranges preferably from room temperature to around 40° C., other temperature conditions are also possible.

The fluorides to be used in the present invention are not particularly limited except for the solubility thereof.

The reason why a difficultly soluble fluoride capable of forming a saturated solution thereof having a fluorine concentration of 1 to 10,000 ppm, preferably 1 to 4,000 ppm, is necessary is that when it is soluble, no precipitate is formed and the colloidization by the peptizer is impossible, and that it is indispensable when the fluoride is used in the form of an oral composition for reinforcing the teeth that it is soluble to some extent to release fluoride ions at a suitable rate.

The soluble fluorides used for the purpose of forming the difficultly soluble fluoride in the present invention are not particularly limited as far as they are capable of releasing fluoride ions. However, sodium fluoride or potassium fluoride which forms a palatable colloidal solution is most suitable for forming the oral composition.

The cations used for the purpose of forming the difficultly soluble fluoride in the present invention are not particularly limited.

The present invention relates to an oral composition comprising three ingredients, i.e. a water-soluble hydrofluoric acid (a first ingredient), a water-soluble calcium salt (a second ingredient) and a peptizer (a third ingredient) which accelerates the colloidization of a reaction product between the first ingredient and the second ingredient.

The fluorine sources usable for producing the colloidal fluoride of the present invention include hydrofluoric acid and pharmacologically acceptable water-soluble hydrofluorides such as sodium fluoride, potassium fluoride, lithium fluoride, ammonium fluoride and tin fluoride. The calcium sources usable herein include water-soluble calcium salts such as chloride, nitrate, acetate, glycerophosphate, glucose 1-phosphate and glucose 6-phosphate.

The particular peptizers usable herein include one or more saccharide derivatives selected from the group consisting of saccharide phosphates such as glyceraldehyde 3-phosphate, α-glycerophosphoric acid, β-glycerophosphoric acid, erythrose 4-phosphate, ribose 5-phosphate, glucose 1-phosphate, glucose 6-diphosphate, inositol monophosphate, inositol hexaphosphate, fructose 1-phosphate, fructose 6-phosphate, fructose 1,6-diphosphate, ascorbic acid 2-phosphate and heptulose 7-phosphate; saccharide sulfates such as sucrose sulfate and ascorbic acid 2-sulfate; glyceric acid and gluconic acid; and salts of them.

When a calcium salt of the saccharide derivative has a high solubility in water, it can serve as both the second ingredient (water-soluble calcium salt) and the third ingredient (peptizer).

When these ingredients are mixed together to give a solution and reacted at room temperature, an extremely fine, stable fluoride colloid can be prepared. The molar proportions of the fluoride ion, the calcium ion and the peptizer are as wide as 0.01 to 1 00/1/0.01 to 100. The molar ratio of fluorine to calcium is desirably as close as the ratio of their stoichiometrical amounts for forming a salt, namely, a ratio of the fluoride ion to the calcium ion of 2/1. The amount of the saccharide derivative is desirably sufficient for stabilizing the colloidal particles. Namely, the ratio of the calcium ion to the peptizer is as close to 1/1 as possible. In due consideration of these requirements, the proportions of the fluoride ion, the calcium ion and the peptizer are particularly preferably 0.1 to 10/1/0.05 to 20. When the ratio of the fluoride ion to the calcium ion in the combination is different from the stoichiometrical ratio for forming a salt, free fluoride ions or calcium ions which do not form colloidal particles are contained in the composition as a matter of course, but such ions do not impair the effect of the present invention.

The above-described colloidal fluoride particles are usually quite fine and the particle diameter is often as small as about 10 nm. A homogeneous colloidal fluoride in the form of a transparent solution can be prepared when the ingredients are used at suitable proportions under suitable conditions Therefore, when the present invention is applied to the production of a transparent mouth-wash or dentifrice, the commercial value thereof can be further increased.

Fluoride ions in the oral composition of the present invention react with calcium ions and a suitable peptizer to form a fluoride colloid having an excellent effect of supplying fluorine to the teeth, whereby the composition has an excellent effect of preventing the tooth from decaying

[EXAMPLE]

The solution will be explained in reference to its examples.

In determination of a fluorine ion concentration, one example is shown below.

Figure 2:
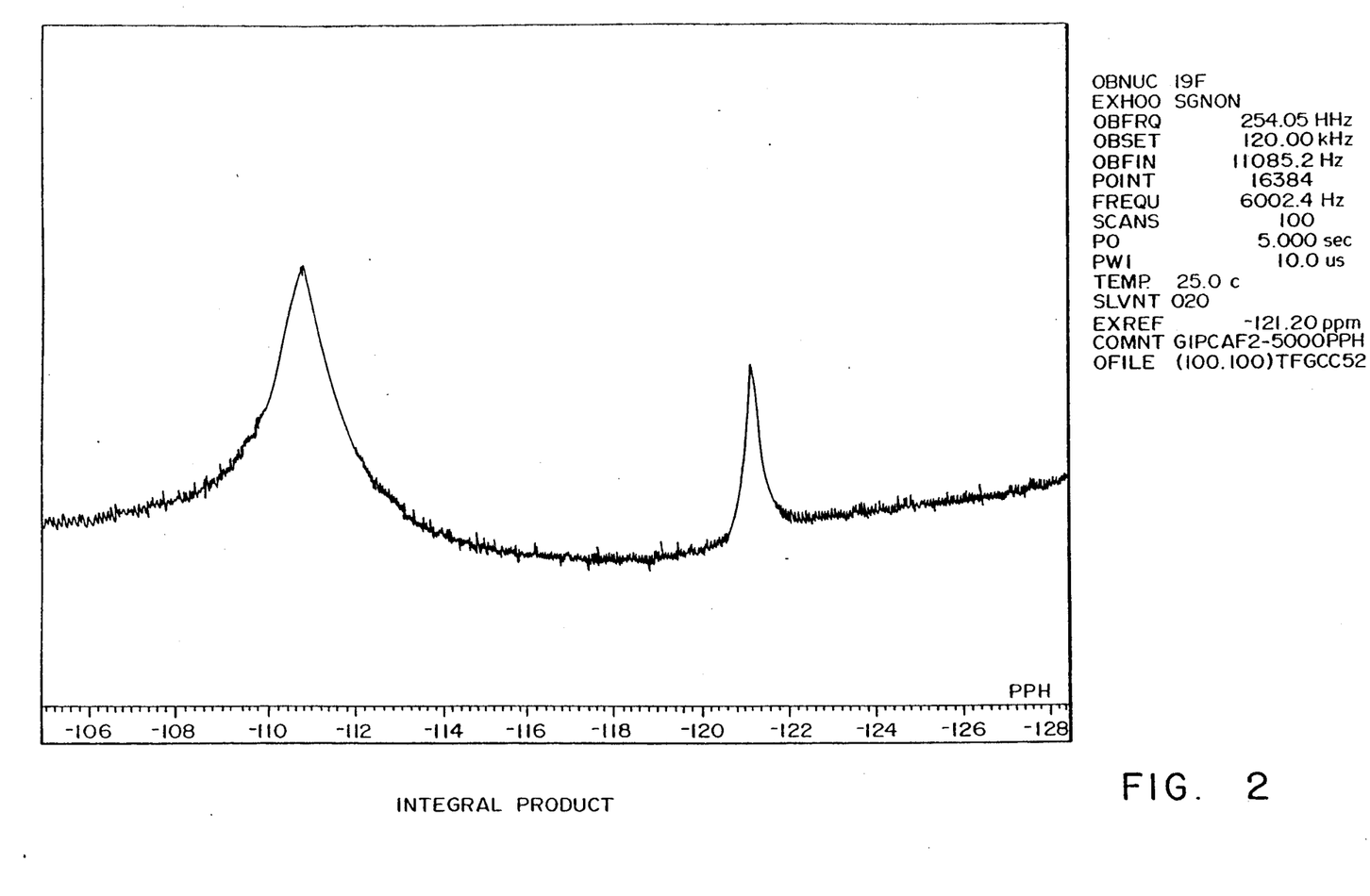
FIGS. 2, 3 and 4 show data for obtaining fluorine amounts.
Figure 3:
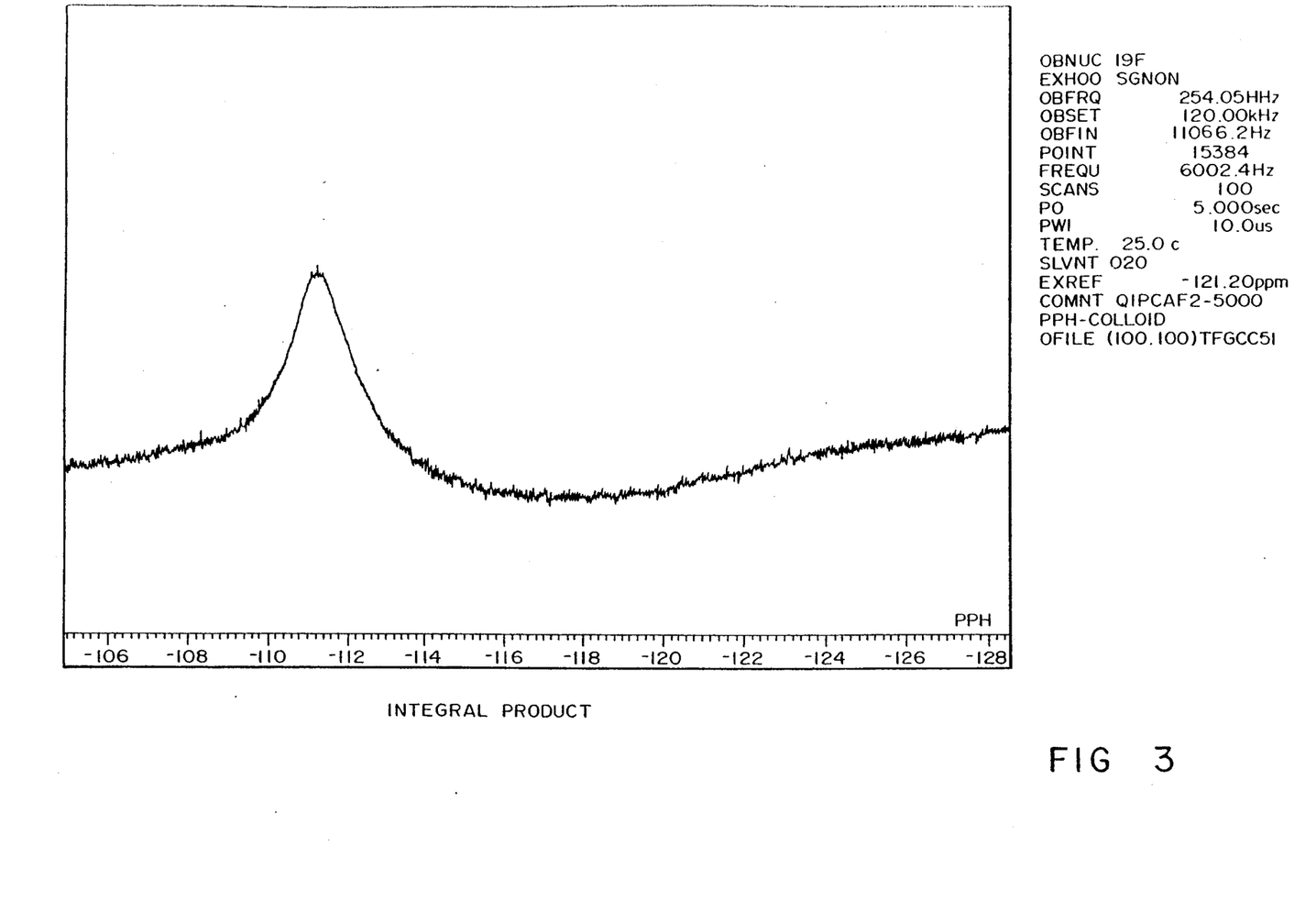
Figure 4:
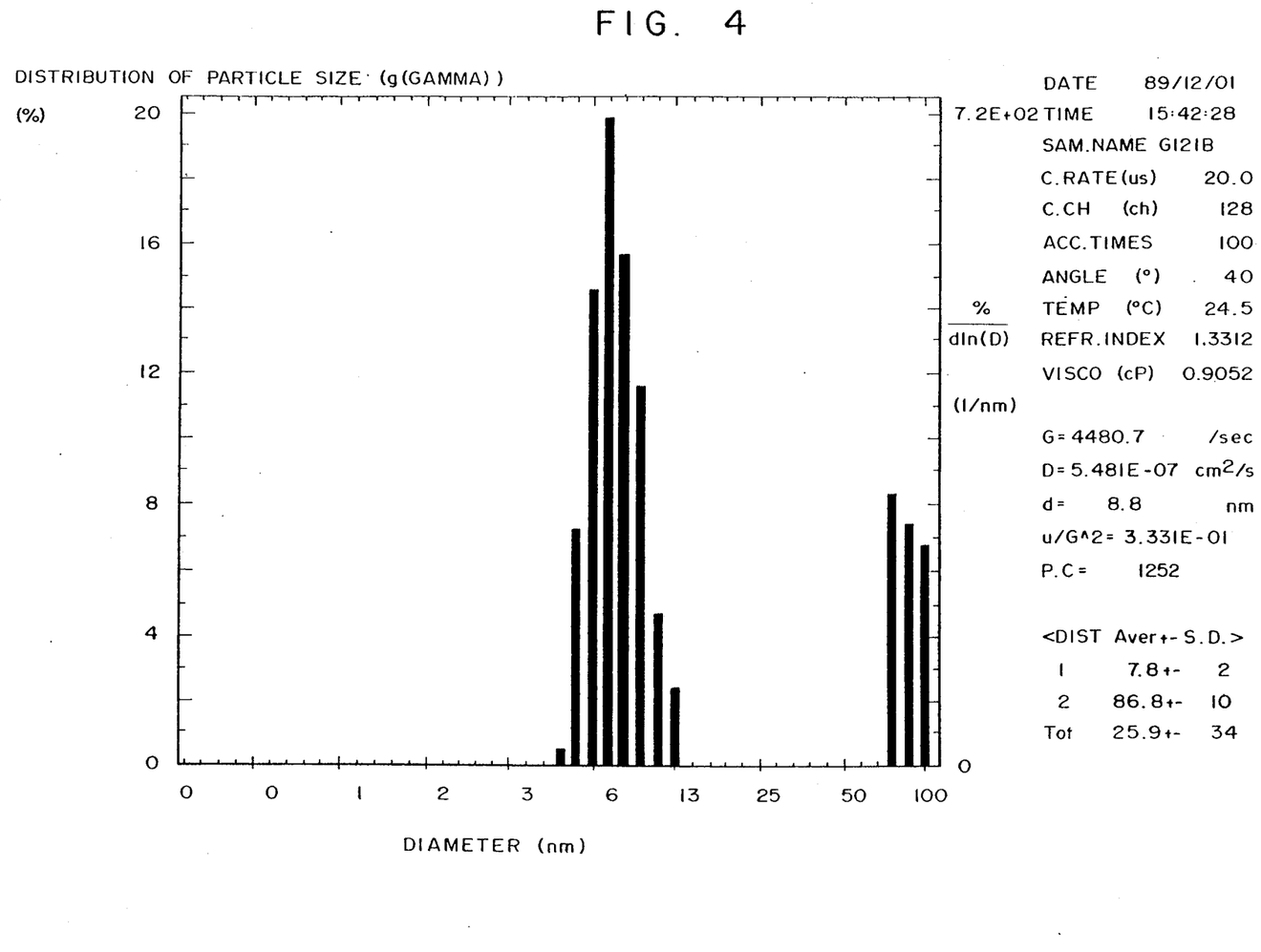

4.87 g of potassium glucose-1-phosphate tetrahydrate, 1.1 g of sodium fluoride and 1.44 g of calcium chloride are added to 100 ml of water. The solution is allowed to stand for 1 day. With the use of $^{19}$F-NMR, JNM GX-270 of Nippon Denshi, a ratio of fluorine in the colloid to fluorine ion in the solution is determined from integral products of their peaks. It is resulted that a ratio of the fluoride in the colloid to the fluorine ion in the solution is found to be 100:0. See FIG. 2. All the used fluoride is distributed to the formed colloids. FIG. 3 shows peaks of fluorine in the colloid and fluorine ion in the solution, respectively, obtained by adding 4.87 g of calcium glucose-1-phosphate tetrahydrate and 1.1 g of sodium fluoride to 100 ml of water and allowing it to stand for 1 day, determined by the above shown NMR. FIG. 4 shows determination of colloidal particles having a size of about 5 nm, obtained by adding calcium glucose-1-phosphate tetrahydrate and sodium fluoride at a mole ratio of 1:2 to water to reach the entire fluorine concentration of 500 ppm and allowing it to stand for 1 day, using the dynamic light scattering method.

Now the description will be made on the effect obtained by applying the colloidal solution of the present invention to teeth.

The present invention has been completed on the basis of a methodology contrary to the prior art wherein efforts were made so that no water-insoluble or difficultly water-soluble precipitate is formed. Namely, the present invention has been completed on the basis of an idea that even when the water-insoluble or difficultly water-soluble precipitate is formed, the effect of the fluoride ion can be maintained as far as the particles thereof are fine. In fact, calcium and fluoride ions in amounts beyond ordinary solubilities were detected in a colloidal solution of calcium fluoride (fine particle solution of the present invention). When the colloidal solution is diluted with water, calcium fluoride is dissolved at a dissolution rate far higher than that of ordinary calcium fluoride to release fluoride ions. An example of this phenomenon is given in Example 1.

EXAMPLE 1

| | F ion | Amount of dissolution |
|---|---|---|
| CaF$_2$ colloid ($\phi$ 0.22 to 0.65 $\mu$m) | 15 | 5 |
| CaF$_2$ colloid (peptizer added) ($\phi$ < 0.22 $\mu$m) | 100 | 20 |
| CaF$_2$ powder (1 to 2 $\mu$m) | 8 | 0.1 |
| CaF$_2$ powder (2 $\mu$m <) | 8 | 0.1 |

Surprisingly, the colloidal particle was one which can be adsorbed on hydroxyapatite which is a constituent of teeth. Thus the effect of retaining fluorine in the mouth was exhibited not only for a short time but also lasted for a long period of time.

The stability of the colloidal solution was remarkably improved by adding the peptizer.

Example 2 gives the results of examination of the state of the colloid and fluorine uptake before and after the storage at room temperature for 6 months.

The colloidal solution was stable also to salts and surfactants usually incorporated into oral compositions. However, it was unstable when the pH was 5.0 or below or 9.0 or above.

[test method]

Calcium glucose-1-phosphate tetrahydrate and sodium fluoride are mixed with each other at a mole ratio of 1:2. Distilled water is added to the mixture to obtain a testing colloidal solution having a fluorine ion concentration of 2,000 ppm.

One gram of hydroxyapatite powder is treated with 10 ml of the solution and then washed with 40 ml of distilled water two times. Three ml of concentrated hydrochloric acid is added to the the powder to obtain its solution, followed by diluting it to a suitable concentration. An amount of the fluoride uptake is determined with the use of a fluoride ion-selective electrode. Results are shown below in Table.

EXAMPLE 2
Effect of disodium glucose 1-phosphate on the state of solution and fluorine uptake effect after storage at room temperature for 6 months

| | Before storage | | After storage | |
|---|---|---|---|---|
| | state | fluorine uptake | state | fluorine uptake |
| Disodium glucose 1-phosphate added | transparent liquid | 6.2 | transparent liquid | 6.1 |
| No disodium glucose 1-phosphate added | bluish white precipitate suspended | 2.3 to 6.3 | white precipitate found at the bottom | <0.1 |

Further the effect of preventing actual teeth from decaying was confirmed.

In the experiment, a nondecayed human tooth was cut into three pieces, and the surface of each piece was polished and manicured, while leaving a part (1 × 1 mm) to be exposed to an acid in each piece. These pieces were immersed in the colloidal solution of the present invention, a sodium fluoride solution, and distilled water, respectively, for 1 min and then delimed with an acid solution.

The colloidal solution and the sodium fluoride solution each contained 100 ppm of fluorine.

The acid solution was adding hydroxyapatite in a concentration of 50% of the saturation to 0.1M lactic acid, further adding 0.2% polyacrylic acid thereto and adjusting the pH to 5.

Since teeth generally becomes cloudy by the deliming, its acid resistance was judged from the extent of formation of white spots in the part exposed to the acid. The white spots were scarcely found in the part which had been treated with the colloidal solution before the exposure to the acid; considerable spots were found in the part which had been treated with distilled water before the exposure to the acid; and some spots were found in the part which had been treated with the NaF solution before the exposure to the acid. Thus an extremely high effect of the treatment with the colloidal solution of the present invention was confirmed.

In addition to the above-described colloidal fluoride solution of the present invention, similar effects can be obtained when other colloidal solutions containing other fluoride and peptizer according to the present invention are used. The state and storage stability of main colloidal fluoride solutions and fluorine uptake effect were examined in Example 3 and the results are summarized in the following table:

The above shown colloid solution was obtained in the same way as shown in Example 1, using the above shown method (ii), at a mole ratio of the peptizer to the cation to sodium fluoride of 1:1:2, having a fluorine ion concentration of 2,000 ppm in the solution. The solution was allowed to stand for 1 day before determination of properties.

The colloidal solution was filtered through a Millipore filter having a pore size of 0.8 micron and the filtrate was centrifuged with an ultracentrifugal separater at 50,000 rpm at 15 degree C. Precipitates

EXAMPLE 3
State and storage stability of main colloidal fluoride solutions and fluorine uptake

| Cation | Peptizer | State and stability (transparency) | | | Confirmation of colloid | Fluorine content of colloidal particles (%) | Fluorine uptake of apatite (mg/g) |
|---|---|---|---|---|---|---|---|
| | | After 6 h | After 1 day | After 1 month | | | |
| Ca | gluconic acid | ○ | △ | X | ○ | 95.3 | 0.84 |
| Ca | glycerophosphoric acid | ○ | ○ | ○ | ○ | 71.4 | 3.08 |
| Ca | ribose 5-phosphate | ○ | ○ | ○ | ○ | 60.0 | 3.00 |
| Ca | glucose 1-phosphate | ○ | ○ | ○ | ○ | 59.0 | 2.24 |
| Ca | glucose 6-phosphate | ○ | ○ | ○ | ○ | 54.0 | 2.20 |
| Ca | sedoheptulose 7-phosphate | ○ | ○ | ○ | ○ | 40.0 | 1.90 |
| Ca | sucrose sulfate | ○ | △ | △ | ○ | 19.0 | 0.70 |
| Mg | glucose 1-phosphate | △ | ○ | ○ | ○ | 32.0 | 1.90 |
| Sr | glucose 1-phosphate | ○ | ○ | ○ | ○ | 18.0 | 0.67 |
| Al | glucose 1-phosphate | △ | △ | △ | ○ | 16.0 | 3.90 |
| Zn | glucose 1-phosphate | △ | △ | △ | X | — | 0.27 |
| Sn | glucose 1-phosphate | ○ | ○ | ○ | X | — | 0.28 |
| Mn | glucose 1-phosphate | ○ | △ | X | ○ | 8.0 | 0.13 |
| Ca | polyphosphoric acid | ○ | ○ | ○ | ○ | 16.0 | 0.08 |
| NaF. | (control) | ○ | ○ | ○ | X | — | 0.11 | found indicate colloidization. A fluorine amount in the colloidal particles is calculated by reducing a fluorine ion amount dissolved in the solution, determined by the fluorine ion electrode, from the entire fluorine amount of the solution. A fluorine amount uptaken by the aperite is determined in the same way as shown in Example 1.

The combinations below the dotted line in the above table are not included in the present invention.

When zinc or tin was used, no colloid was formed.

When manganese was used, the fluorine uptake effect was similar to that of the control, though the colloid was formed.

Colloids superior to the fluorine-containing agents heretofore used were those having a fluorine content of the colloidal particles of at least 10%.

The colloid containing strontium in Example 3 had a fluorine content in the colloidal particles of 18% and fluorine uptake of 6 times as high as that of the control and, therefore, it is superior to the fluorine-containing agents heretofore used.

Although polyphosphoric acid serves as the peptizer, it does not seem to be adsorbable on teeth.

The fluorine intakes of the controls were far lower than those of the colloidal solutions of the present invention.

The colloidal solution of the present invention is used singly or in combination with other substances so as to have a fluorine content of 10 to 100,000 ppm, or the composition thus formed can be supported on another carrier to form an oral composition usable for preventing the tooth from decaying.

Application Examples of the colloidal solution of the present invention will now be described.

EXAMPLE 4
(mouth-wash)

| | |
|---|---|
| glycerol | 20.0% by weight |
| sorbitol | 24.0% by weight |
| propylene glycol | 3.0% by weight |
| polyoxyethylene polyoxypropylene glycol | 1.0% by weight |
| methyl p-hydroxybenzoate | 0.1% by weight |
| saccharin sodium | 1.0% by weight |
| flavor | 0.9% by weight |
| colloidal solution (Note 1) | 50.0% by weight |
| | 100.0% by weight |

(Note 1) A 3 mM solution of calcium chloride or strontium chloride was prepared and an equal amount 6 mM sodium fluoride was added to this solution. Immediately thereafter, 1M slurry of disodium glycerophosphate or disodium ribose 5-phosphate was added dropwise thereto to make the mixture transparent. The transparent mixture was left to stand for 1 h and used for the formulation.

EXAMPLE 5
(tablets for mouth-wash) (Note 1)

| | |
|---|---|
| dry fluoride gel (Note 2) | 25.0% by weight |
| common salt | 68.0% by weight |
| hydroxyethylcellulose | 1.0% by weight |
| saccharin sodium | 5.0% by weight |
| flavor | 1.0% by weight |
| | 100.0% by weight |

(Note 1) A tablet weighing 5 g is dissolved in 100 ml of water or hot water for use as a mouthwash.
(Note 2) 12 g of aluminum chloride and 18 g of disodium glucose 1-phosphate tetrahydrate were added to 4.2 g of sodium fluoride. 100 ml of water was added to the mixture and stirred to give a transparent mixture. It was centrifuged with a centrifugal separator (200,000 G) for 10 h and a precipitate thus formed was dried and pulverized.

EXAMPLE 6
(tooth paste)

| | |
|---|---|
| abrasive (Note 1) | 40.0% by weight |
| glycerol | 20.0% by weight |
| sorbitol | 24.0% by weight |

-continued

| | |
|---|---|
| propylene glycol | 3.0% by weight |
| hydroxyethylcellulose | 1.0% by weight |
| sodium lauryl sulfate | 1.0% by weight |
| methyl p-hydroxybenzoate | 0.1% by weight |
| saccharin sodium | 1.0% by weight |
| flavor | 0.9% by weight |
| dry fluoride gel (Note 2) | 1.0% by weight |
| | 100.0% by weight |

(Note 1) Either calcium hydrogenphosphate dihydrate or calcium pyrophosphate was used.
(Note 2) The same as the dry gel in (Note 2) of Application Example 2.

The oral composition will be explained in reference to its tests and examples.

The effect of the present invention will be further illustrated by the following Experimental Examples of the production of the colloidal fluoride which can be contained in the oral composition of the present invention and Experimental Examples of evaluation of its capacity of supplying fluorine to the tooth.

Experiment 1

[dissolution state of solution of mixture of fluorine, calcium and peptizer and colloid formation]

A mixture of predetermined amounts of sodium fluoride as the fluorine source and calcium glucose 1-phosphate as both the calcium source and peptizer source, or calcium chloride as the control was dissolved in purified water to give a predetermined mixing ratio. The solution was left to stand at room temperature for one day and a precipitate thus formed was observed. The mixing molar proportions of the fluoride ion, the calcium ion and the glucose 1-phosphate ion were 0.1 to 10:1:0 to 1. The total fluorine concentration in the solution was 50 to 5,000 ppm.

TABLE 1

Precipitate formation from solution of mixture of sodium fluoride and calcium glucose 1-phosphate

| Total fluorine concn. (ppm) | F:Ca:GlP (molar ratio) | | | | | | |
|---|---|---|---|---|---|---|---|
| | 0.1:1:1 | 0.4:1:1 | 1:1:1 | 2:1:1 | 4:1:1 | 10:1:1 | 2:1:0 |
| 8 | − | − | − | − | − | − | − |
| 50 | − | − | − | − | − | − | ± |
| 150 | − | − | − | − | − | − | ++ |
| 500 | ± | − | − | − | − | − | ++ |
| 1500 | ++ | ± | − | − | − | ± | +++ |
| 5000 | +++ | ++ | ++ | − | ++ | ++ | +++ |

GlP: glucose 1-phosphate.
+++: precipitate formation remarkable.
++: a relatively large amount of precipitates formed.
±: only a small amount of precipitates formed.
−: no precipitate formed.

The particle diameter in a solution having the best dissolution state (F/Ca/GlP=2/1/1) and having a fluorine concentration of 1500 ppm was determined with a dynamic light scattering measurement device (mfd. by Otsuka Denshi) to reveal that the particles were extremely fine colloidal particles having a mean particle diameter of 12.5 nm. The calcium ion concentration was measured with an ion-selective electrode (mfd. by Orion) to find that the free calcium ion concentration therein was less than 1 mM. Namely, substantially free calcium ion was not present therein. This fact suggests that calcium present in the solution is substantially in the form of colloidal particles and is no more in the form of an ion.

In another solution wherein Fa/Ca was 0.1 to 1/1, the calcium ion concentration was reduced as the total fluorine concentration was increased. In still another solution wherein F/Ca was 4 to 10/1, substantially no calcium ion was present. Although a small amount of the precipitate is found in the solution containing glucose 1-phosphate, its amount is smaller than that of the precipitate formed in the control solution free from glucose 1-phosphate. It is evident from this fact that at least part of calcium forms colloidal particles in the presence of glucose 1-phosphate.

Experiment 2

[effect of fluoride colloid of supplying fluorine to tooth]

In this experiment, hydroxyapatite (a calcium phosphate constituting at least 90% of the enamel of the tooth) powder was used as a model tooth. 1 g of the powder was dispersed in 10 ml of deionized water and 30 ml of a colloidal fluoride solution (F/Ca/GlP=2/1/1) having a varied concentration was added to the dispersion. The mixture was treated at room temperature for one minute and then centrifuged at 3,000 rpm to give hydroxyapatite powder, which was then washed by dispersing in pure water. This procedure was repeated again. The powder was dissolved in 3 ml of concentrated hydrochloric acid and the solution was suitably diluted. The quantity of fluorine taken therein was determined with an ion-selective electrode.

Figure 1:
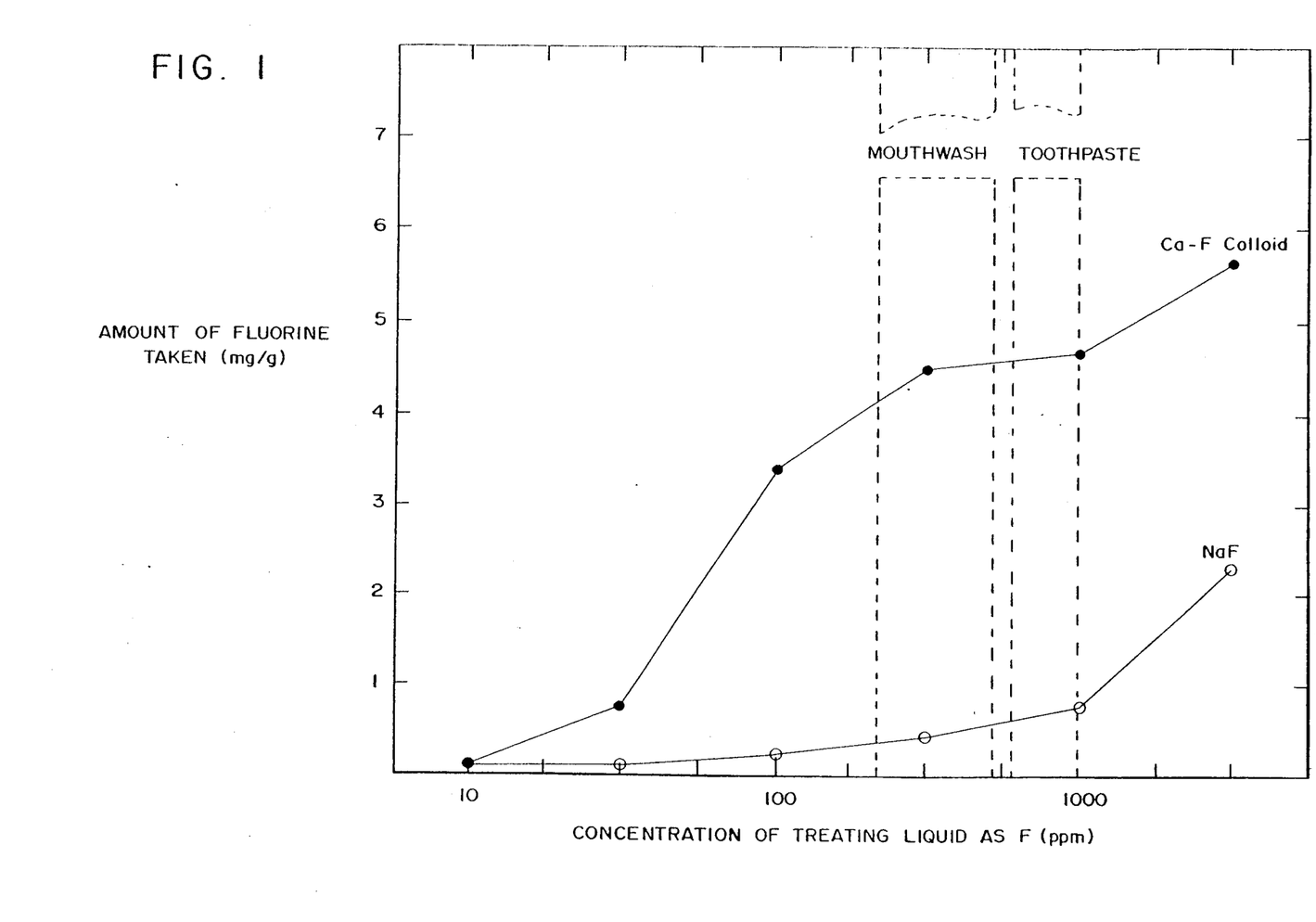
FIG. 1 is a graph showing the effect of the invention.

FIG. 1 is a graph showing changes in the quantity of fluorine taken into hydroxyapatite when a colloidal fluoride solution or a sodium fluoride solution (control) was used and the total fluorine concentration in the solution was varied from 10 to 3,300 ppm. It is apparent from the graph that when the fluorine concentration was adjusted to that of ordinary dentifrices or mouthwashes, the colloidal fluoride had at least 10 times as high fluorine-supplying capacity as that of sodium fluoride.

Experiment 3

[effect of colloidal fluoride of improving acid resistance of tooth]

A sound human tooth was vertically divided into three pieces, polished on the surface and were each coated with an oil-base paint in order to keep the tooth from attack by an acid, while leaving a part (about 1×1 mm) of the enamel to form a window to be exposed to the acid. Then the sample tooth pieces were immersed in a colloidal fluoride solution (F/Ca/GlP=2/1/1) having a total fluorine concentration of 100 ppm, a sodium fluoride solution having a total fluorine concentration of 100 ppm, and deionized water (control), respectively, at room temperature for 1 min to treat the exposed surface of the enamel therewith. Then each sample was immersed in a 0.1M lactate buffer solution (pH: 5.0) at room temperature for 12 h to delime the exposed part of the enamel. This procedure was continuously repeated six times. Then the paint was removed and white spots (initial stage of tooth decaying) formed in the delimed part were observed. Thus it was found that the extent of the formation of the white spots were as follows: sample treated with deionized water > sample treated with sodium fluoride > sample treated with colloidal fluoride. This fact indicated that the colloidal fluoride had an excellent effect of improving the acid resistance of the tooth. The above shown 0.1M lactate buffer is obtained by the following. One percent of Carbopol 907, tradename of polyacrylic acid, is adjusted at pH of 4.0. with 10N NaOH. 40 ml of the liquid is mixed with 2 g of lactic acid and then distilled water to amount to 200 ml, adjusted at pH of 5.0 with 10N NaOH, to obtain an unsaturated liquid of apatite. 110 ml of the liquid is mixed with 0.22 g of hdyroxyapatite. The mixture is adjusted at pH of 5.0 with 1N hydrochloric acid and centifuged, decanted. The decanted liquid is filterated with a Millipore filter having a pore size of 1 micron to obtain saturated apatite solution. It is mixed equivoquantatively with the unsaturated apatite solution to obtain 0.1M lactate solution.

Experiment 4

[peptizers]

In this experiment sodium fluoride, calcium chloride and each of the sodium salts of various saccharide derivatives were mixed together in a molar proportion of 2/1/1 so that the total fluorine concentration would be 500 ppm to give a solution. One day after, the state of the solution (refer to Experiment 1) was observed with naked eyes and the effect of supplying fluorine (refer to Experiment 2) was evaluated.

TABLE 2

Function of various saccharide derivatives as the peptizer

| Peptizer | State of solution (precipitate formation) | Supply of fluorine (mg/g) |
| --- | --- | --- |
| glyceraldehyde 3-phosphate | — | 1.2 |
| α-glycerophosphate | — | 1.7 |
| β-glycerophosphate | — | 3.1 |
| erythrose 4-phosphate | — | 2.2 |
| ribose 5-phosphate | — | 2.8 |
| glucose 1-phosphate | — | 4.2 |
| glucose 6-diphosphate | — | 3.8 |
| inositol monophosphate | — | 2.5 |
| inositol hexaphosphate | — | 1.3 |
| fructose 1-phosphate | — | 2.5 |
| fructose 6-phosphate | — | 1.6 |
| fructose 1,6-diphosphate | — | 1.0 |
| ascorbic acid 2-phosphate | — | 2.0 |
| heptulose 7-phosphate | — | 1.7 |
| sucrose sulfate | + | 1.0 |
| ascorbic acid 2-sulfate | + | 1.1 |
| glyceric acid | + | 0.6 |
| gluconic acid | + | 0.8 |
| control (no peptizer used) | ++ | 0.3 |

The above-described results indicate that not only glucose 1-phosphate but also many kinds of saccharide derivatives act as the peptizer to form a colloidal fluoride in the same manner.

It is apparent from the above-described experiments that when a fluoride ion is reacted with a calcium ion in the presence of a particular saccharide derivative, the colloidal fluoride having an excellent effect of supplying fluorine to the tooth can be formed. It is necessary, however, that the total fluorine concentration in the solution exceed 8 ppm, since the fluorine concentration of a saturated calcium fluoride solution is about 8 ppm. When the total fluorine concentration is less than 8 ppm, calcium fluoride is dissolved and no colloidal fluoride can be formed.

Although the saccharide derivative used in the above-described experiment was the sodium salt, a calcium salt of the saccharide derivative can also be used if it is highly soluble in water. The calcium salts include calcium glucose 1-phosphate, calcium glucose 6-phosphate and calcium fructose 1,6-diphosphate. When such a calcium salt is used, the incorporation of an additional water-soluble calcium salt is not always necessary.

The colloidal fluoride solution can be used as an oral composition in various forms such as a dentifrice, a mouth-wash, a tooth coating agent, buccal tablets and chewing gum. Various bases and other medicinal ingredients usually incorporated into dentifrices, mouth-washes, agents to be applied to the tooth and buccal tablets can be also incorporated thereinto. However, when a compound having a strong chelating effect or an ingredient easily adsorbable on calcium phosphate is used, attention should be paid not to lose the effect of the colloidal fluoride, since it might destroy the colloidal fluoride or aggregate the colloidal particles to form a precipitate.

The following Examples of the composition of the present invention comprising the colloidal fluoride and effective in preventing the tooth from decaying further illustrate the present invention, a which by no means limit the invention.

EXAMPLE 7

(toothpaste)

Among the following ingredients, sodium fluoride and calcium glucose 1-phosphate were first dissolved in purified water to form a fluoride colloid. Then other ingredients were mixed with the colloid under deaeration to form a toothpaste. The effect of the toothpaste of preventing the tooth from initial decaying was evaluated by the method employed in Experiment 3. The results indicated an excellent effect thereof.

| | |
| --- | --- |
| sodium fluoride | 0.2% by weight |
| calcium glucose 1-phosphate tetrahydrate | 0.9% by weight |
| aluminum hydroxide | 35.0% by weight |
| hydroxyethylcellulose | 2.0% by weight |
| sucrose fatty acid ester | 2.5% by weight |
| fatty acid diethanolamide | 0.5% by weight |
| glycerol | 10.0% by weight |
| 70% sorbitol solution | 15.0% by weight |
| methylparaben | 0.1% by weight |
| flavor | 1.0% by weight |
| sodium saccharin | 0.2% by weight |
| purified water | a suitable amount |
| total | 100.0% by weight |

EXAMPLE 8

(toothpaste)

Among the following ingredients, sodium fluoride and calcium glucose 1-phosphate were dissolved in purified water to form a fluoride colloid. Then other ingredients were mixed with the colloid under deaeration to form a toothpaste in the form of a transparent gel. The effect of the toothpaste of preventing the tooth from initial decaying was evaluated by the method employed in Experiment 3. The results indicated an excellent effect thereof.

| | |
| --- | --- |
| sodium fluoride | 0.2% by weight |
| calcium glucose 1-phosphate tetrahydrate | 2.0% by weight |
| silicic acid anhydride | 25.0% by weight |
| polysodium acrylate | 1.0% by weight |
| hydroxyethylcellulose | 1.0% by weight |
| sodium lauryl sulfate | 1.5% by weight |
| glycerol | 10.0% by weight |
| 70% sorbitol solution | 15.0% by weight |

| | |
|---|---|
| methylparaben | 0.1% by weight |
| flavor | 1.0% by weight |
| sodium saccharin | 0.2% by weight |
| colorant | a suitable amount |
| purified water | a suitable amount |
| total | 100.0% by weight |

EXAMPLE 9

(toothpaste)

Among the following ingredients, potassium fluoride and calcium glycose 6-phosphate were dissolved in purified water to form a fluoride colloid. Then other ingredients were mixed with the colloid under deaeration to form a toothpaste. The effect of the toothpaste of preventing the tooth from initial decaying was evaluated by the method employed in Experiment 3. The results indicated an excellent effect thereof.

| | |
|---|---|
| potassium fluoride | 0.2% by weight |
| calcium glucose 6-phosphate tetrahydrate | 2.0% by weight |
| calcium hydrogenphosphate for dentifrice | 25.0% by weight |
| sodium carboxymethylcellulose | 1.0% by weight |
| hydroxyethylcellulose | 1.0% by weight |
| soidum lauryl sulfate | 1.5% by weight |
| fatty acid diethanolamide | 0.5% by weight |
| glycerol | 10.0% by weight |
| 70% sorbitol solution | 15.0% by weight |
| methylparaben | 0.1% by weight |
| flavor | 1.0% by weight |
| sodium saccharin | 0.2% by weight |
| purified water | a suitable amount |
| total | 100.0% by weight |

EXAMPLE 10

(toothpaste)

Among the following ingredients, sodium fluoride and calcium fructose 1,6-diphosphate were first dissolved in purified water to form a fluoride colloid. Then other ingredients were mixed with the colloid under deaeration to form a toothpaste. The effect of the toothpaste of preventing the tooth from initial decaying was evaluated by the method employed in Experiment 3. The results indicated an excellent effect thereof.

| | |
|---|---|
| sodium fluoride | 0.2% by weight |
| calcium fructose 1,6-diphosphate | 0.5% by weight |
| crystalline cellulose powder | 15.0% by weight |
| sodium carboxymethylcellulose | 1.0% by weight |
| hydroxyethylcellulose | 1.0% by weight |
| sodium lauryl sulfate | 1.5% by weight |
| fatty acid diethanolamide | 0.5% by weight |
| glycerol | 10.0% by weight |
| 70% sorbitol solution | 15.0% by weight |
| methylparaben | 0.1% by weight |
| flavor | 1.0% by weight |
| sodium saccharin | 0.2% by weight |
| purified water | a suitable amount |
| total | 100.0% by weight |

EXAMPLE 11

(mouth-wash)

The following ingredients were mixed together to form a solution to be used as a mouth-wash. The effect of the mouth-wash of prevention the tooth from initial decaying was evaluated by the method employed in Experiment 3. The results indicated an excellent effect thereof.

| | |
|---|---|
| sodium fluoride | 0.2% by weight |
| calcium glucose 1-phosphate tetrahydrate | 1.0% by weight |
| glycerol | 5.0% by weight |
| polyoxyethylene-hardened castor oil | 0.5% by weight |
| ethanol | 8.0% by weight |
| sodium saccharin | 0.1% by weight |
| flavor | 0.1% by weight |
| colorant | a suitable amount |
| purified water | a suitable amount |
| total | 100.0% by weight |

EXAMPLE 12

(mouth-wash)

The following ingredients were mixed together to form a solution to be used as a mouth-wash. The effect of the mouth-wash of preventing the tooth from initial decaying was evaluated by the method employed in Experiment 3. The results indicated an excellent effect thereof.

| | |
|---|---|
| sodium fluoride | 0.2% by weight |
| calcium glucose 6-phosphate | 1.5% by weight |
| calcium chloride dihydrate | 0.2% by weight |
| glycerol | 5.0% by weight |
| polyoxyethylene-hardened castor oil | 0.5% by weight |
| ethanol | 8.0% by weight |
| sodium saccharin | 0.1% by weight |
| flavor | 0.1% by weight |
| colorant | a suitable amount |
| purified water | a suitable amount |
| total | 100.0% by weight |

EXAMPLE 13

(mouth-wash)

The following ingredients were mixed together to form a solution to be used as a mouth-wash. The effect of the mouth-wash of preventing the tooth from initial decaying was evaluated by the method employed in Experiment 3. The results indicated an excellent effect thereof.

| | |
|---|---|
| sodium fluoride | 0.2% by weight |
| sodium ribose 5-phosphate | 2.0% by weight |
| calcium chloride dihydrate | 0.3% by weight |
| glycerol | 5.0% by weight |
| polyoxyethylene polypropylene glycol | 0.8% by weight |
| ethanol | 8.0% by weight |
| sodium saccharin | 0.1% by weight |
| flavor | 0.1% by weight |
| colorant | a suitable amount |
| purified water | a suitable amount |
| total | 100.0% by weight |

EXAMPLE 14

(tooth coating agent)

The following ingredients were mixed together to form a viscous tooth coating agent. The effect of this agent of preventing to tooth from initial decaying was evaluated by the method employed in Experiment 3. The results indicated an excellent effect thereof.

| | |
|---|---|
| sodium fluoride | 2.0% by weight |
| calcium glucose 1-phosphate tetrahydrate | 9.0% by weight |
| hydroxyethylcellulose | 2.0% by weight |
| flavor | a suitable amount |
| purified water | a suitable amount |
| total | 100.0% by weight |

EXAMPLE 15

(buccal tablets)

2 mol of sodium fluoride was mixed with 1 mol of calcium glucose 1-phosphate powder and purified water was added to the mixture to form a colloidal solution having a high concentration, i.e., a solute concentration of 50 wt. %. Ethanol was added thereto in a volume equal to that of the solution to precipitate the fluoride colloid, which was recovered by filtration and dried to give a dry powder comprising fluoride colloid particles.

Then the following ingredients were mixed with the powder, and the mixture was dry-tabletted to form buccal tablets. The buccal tablets thus formed were pulverized and dispersed in purified water to form a 20% dispersion. The effect of this dispersion of preventing the tooth from initial decaying was evaluated by the method employed in Experiment 3. The results indicated an excellent effect thereof.

| | |
|---|---|
| dry powder of fluoride colloid particles | 1.0% by weight |
| dextrin | 10.0% by weight |
| sodium saccharin | 0.5% by weight |
| citric acid | 0.1% by weight |
| flavor | a suitable amount |
| purified water | a suitable amount |
| total | 100.0% by weight |

EXAMPLE 16

(chewing gum)

The dry powder comprising fluoride colloid particles prepared in Example 15 was kneaded together with ingredients listed below under heating and the mixture was shaped into a chewing gum. 10 g of the chewing gum was finely broken in 50 ml of purified water to form a dispersion. The effect of this dispersion of preventing the tooth from initial decaying was evaluated by the method employed in Experiment 3. The results indicated an excellent effect thereof.

| | |
|---|---|
| dry powder of fluoride colloid particles | 1.0% by weight |
| gum base | 20.0% by weight |
| corn syrup | 20.0% by weight |
| citric acid | 0.1% by weight |
| flavor | a suitable amount |
| sucrose powder | a suitable amount |
| total | 100.0% by weight |

We claim:

1. A colloidal tooth decay preventing fluoride dentrifice or mouthwash comprising colloidal particles of fluoride which are difficulty soluble in water, said colloidal particles of fluoride having a particle size of 0.005 to 1 micron, said fluoride having a fluoride ion concentration of 1 to 10,000 ppm in the state of saturation.

2. The dentrifice or mouthwash as claimed in claim 1, comprising at least one peptizer to colloidize said fluoride.

3. The dentrifice or mouthwash as claimed in claim 1, which comprises 1 to 100,000 ppm, based on the entire solution, of fluorine in said colloidal particles, 10 to 100 percent by weight of the fluorine contained in said solution being included in said colloidal particles.

4. The dentrifice or mouthwash as claimed in claim 2, in which said peptizer is selected from the group consisting of a polyolphosphoric acid, a polyolsulfuric acid, a polyolcarboxylic acid and salts thereof.

5. The dentrifice or mouthwash as claimed in claim 1, which comprises 1 to 95,000 ppm, based on said solution, of fluorine in said colloidal particles, 10 to 95 percent by weight of said fluorine contained in said solution being included in the colloidal particles.

6. The dentrifice or mouthwash as claimed in claim 1, wherein said colloidal particles of said fluoride have a particle size of 0.005 to 1 micron.

7. A colloidal tooth decay preventing fluoride dentrifice or mouthwash or buccal tablet or chewing gum which comprises at least one water-soluble fluoride, at least one water-soluble cationic salt and at least one peptizer.

8. The dentrifice or mouthwash or buccal tablet or chewing gum as claimed in claim 7, wherein said at least one fluoride is a water-soluble hydrofluoric acid and said at least one water-soluble cationic salt is a water-soluble calcium salt.

9. The dentrifice or mouthwash or buccal tablet or chewing gum as claimed in claim 7, wherein said peptizer is a saccharide selected from a monosaccharide having 3 to 10 carbon atoms and one or more phosphate groups and/or sulfate groups and/or carboxyl groups in the molecule, an oligosaccharide comprising 2 to 6 of the monosaccharide and a saccharide which is a polyhydric alcohol having 3 to 10 carbon atoms.

10. The dentrifice or mouthwash or buccal tablet or chewing gum as claimed in claim 7, which comprises at least 10 ppm of fluorine.

11. The dentrifice or mouthwash or buccal tablet or chewing gum as claimed in claim 7, which comprises 10 ppm to 100,000 ppm of fluorine.

12. The dentrifice or mouthwash or buccal tablet or chewing gum as claimed in claim 7, which comprises 150 ppm to 60,000 ppm of fluorine.

13. The dentrifice or mouthwash or buccal tablet or chewing gum as claimed in claim 7, which comprises 1 mol part of the calcium, 0.01 to 100 mol parts of the fluorine and 0.01 to 100 mol parts of the saccharide.

14. The dentrifice or mouthwash or buccal tablet or chewing gum as claimed in claim 7, which comprises 1 mole part of the calcium, 0.1 to 10 mol parts of the fluorine and 0.1 to 10 mol parts of the saccharide.

* * * * *